United States Patent [19]
Steiner

[11] Patent Number: 6,020,128
[45] Date of Patent: Feb. 1, 2000

[54] DNA POLYMERASE FROM *TREPONEMA PALLIDUM*

[75] Inventor: Bret Martin Steiner, Atlanta, Ga.

[73] Assignee: United States of Ameria, Washington, D.C.

[21] Appl. No.: 08/872,094

[22] Filed: Jun. 10, 1997

[51] Int. Cl.[7] .............................. C12Q 1/68; C12N 9/12; C07H 21/04; C07H 21/02
[52] U.S. Cl. ............................ 435/6; 435/194; 536/23.1; 536/23.2; 536/24.3; 536/24.32
[58] Field of Search ...................... 435/6, 194; 536/23.2, 536/24.3, 24.32, 23.1

[56] References Cited

U.S. PATENT DOCUMENTS

| | | | |
|---|---|---|---|
| 4,868,118 | 9/1989 | Norgard | 435/252.33 |
| 5,350,842 | 9/1994 | Norgard | 536/23.7 |
| 5,508,168 | 4/1996 | Orle et al. | 435/6 |

FOREIGN PATENT DOCUMENTS 9112326  8/1991  WIPO .

OTHER PUBLICATIONS

Steiner et al, Genbank Accession No. U57757, published Oct. 25, 1996.

"Detection of *Treponema pallidum* in Early Syphilis by DNA Amplification", Konrad Wicher et al., *Journal of Clinical Microbiology*, Feb. 1992, vol. 30, No. 2, pp. 497–500.

"Use of Polymerase Chain Reaction and Rabbit Infectivity Testing to Detect *Treponema pallidum* in Amniotic Fluid, Fetal and Neonatal Sera, and Cerebrospinal Fluid", Emmanuel Grimprel et al., *Journal of Clinical Microbiology*, Aug. 1991, vol. 9, No. 8, pp. 1711–1718.

"Detection by Polymerase Chain Reaction of *Treponema pallidum* DNA in Cerebrospinal Fluid from Neurosyphilis Patients before and after Antibiotic Treatment", Noordhoek et al., *Journal of Clinical Mcirobiology*, Sep. 1991, vol. 29, No. 9, pp. 1976–1984.

"Simultaneous PCR Detection of *Haemophilus decreyi, Treponema pallidum*, and Herpes Simplex Virus Types 1 and 2 from Genital Ulcers", Orle et al., *Journal of Clinical Microbiology*, Jan. 1996, vol 34, No. 1, pp. 49–54.

"Use of polymerase chain reaction to detect DNA sequences specific to pathogenic treponemes in cerebrospinal fluid", Hay et al., *FEMS Microbiology Letters 68*, Mar. 15, 1990, vol. 68/3 pp. 233–238.

*Primary Examiner*—Bradley Sisson
*Assistant Examiner*—Einar Stole
*Attorney, Agent, or Firm*—Jones & Askew, LLP

[57] ABSTRACT

The nucleic acid sequence encoding the gene for the DNA polymerase I enzyme of *Treponema pallidum*, the organism causing syphilis. Nucleic acid molecules useful as probes for detecting *Treponema pallidum* are described. Isolated, recombinant, and synthetic DNA polymerase I enzyme of *Treponema pallidum*, and the amino acid sequence of the enzyme, are also described. Antibodies to DNA polymerase I from *Treponema pallidum* are further provided. The nucleic acid molecules are useful in methods for the detection and diagnosis of *Treponema pallidum* infection in a sample or subject.

17 Claims, 2 Drawing Sheets

Figure 1

MLHITLSLRLTVVYSLHLMQEKKTLYLLDAYGLIYRSYHAFARAPLINDSGANVSAVYGFFRSLHT

LLCHYRPRYFVAVFDSLTPTFRHVQYPAYKAKRDKTSAELYAQIPLIEEILCALGITVLRHDGFEAD

DLIATLAKRVAAEHCHVVIISSDKDVLQLVCDTVQVLRLDIDHKWTCCDAAYVQQRWTVMPTQLL

DLFSLMGDSSDNVPGVRGIGPKTAAHLLHCFGTLDGIYRHTYSLKEALRTKIVCGKKDAFFSRSLIE

LRDDVPCVFSL<u>EDSCCIPL</u>DVTSAARIFVREGLHALAQQYRACVQEIDTEATNDTLQMTESSVLTS
        Primer 1
GRCANEC<u>FLSQVEGRASTPEVNSVLKSELKTSAVSGAIPIENRDLRQDVMLAR</u>SAGHYRGVTDP
    Primer 3
VELKRII<u>DCACANGVVAFDCETDGLHPHDTRLVGFSICFQEAEAFYVPL</u>I<u>VPDVSLH</u><u>TESTQCTC</u>
       Primer 2                                  Primer 4
<u>ARSTNVETEKECTEQHGVSASAV</u>QDPAYVQAVMHQLRRLWNDETLTLVMHNGKFDYHVMHRAG

VFEHCACNIFDTMVAAWLLDPDRGTYGMDVLAASFFQIRTITFEEVVAKGQTFAHVPYECAVRYA

AEDADITFRLYHYLKLRLETAGLLSVFETIEMPLLPILARMEEVGIFLRKDVVQQLTRSFSDLIQQYE

HDIFSLAGHEFNIGSPKQLQTVLFQELHLPPGKKNTQGYSTDHSVLKKLARKHPIAEKILLFRDLSKL

RSTYTESLAKLADQTGRVHTSFVQIGTATGRLSSRNPNLQNIPIKSTEGRKIRQAFQATVGHELISAD

YTQIELVALAHLSQDRNLLNAFRQHIDIHALTAAYIFNVSIDDVQPAMRRIAKTINFGIVYGMSAFRL

SDELKISQKEAQSFIYRYFETYPGVYAFSTQVAEQTRKTGYVTSLAGRRRYIRTIDSRNTLERARAE

RMALNTQIQSSAADIVKIAMIAIQRAFARRPLRAQLLLQVHDELIFEAPAAETAIVKEILFAEMEHA

VELSIPLRIHVESGNSWGDFH

Figure 2

| 1 | PstI clone; bp 858-2578 | |
| | ClaI clone (Tp615); bp 1625-3238 | 2 |

Figure 3

Primer 1
TGC GCG TGT GCG AAT GGT GTG GTC          (SEQ ID NO: 4)

Primer 2
CAC AGT GCT CAA AAA CGC CTG CAC G        (SEQ ID NO: 5)

Primer 3
TGT TTC TTA TCT CAG GTA GAA GGG          (SEQ ID NO: 6)

Primer 4
ACA TGT ACA CTG AGT TGA CTC GG           (SEQ ID NO: 7)

DNA POLYMERASE FROM *TREPONEMA PALLIDUM*

This invention was made by the Centers for Disease Control, an agency of the United States Government.

TECHNICAL FIELD

The present invention relates in general to the fields of enzymology and diagnostic microbiology. In particular, the invention relates to a novel DNA polymerase gene, its sequence and product, and the detection of syphilis using DNA probes and primers therefrom.

BACKGROUND OF THE INVENTION

DNA polymerase I, the product of the PolA gene, is an important enzyme involved in both DNA repair and semi-conservative DNA replication, in which the enzyme provides gap filling on the lagging strand. Besides its considerable biological interest, DNA polymerase I has engendered much research in terms of commercial applications. For example, the enzyme from *E. coli*, in the form of the Klenow fragment, is an essential reagent in molecular cloning since it is necessary for tasks such as the end filling of restriction fragments and other forms of gap filling. In addition, thermostabile DNA polymerase I genes are necessary for techniques and procedures involving the polymerase chain reaction (PCR).

Syphilis is an infectious venereal disease caused by the spirochete, *Treponema pallidum*. Syphilis is usually transmitted by sexual intercourse or acquired congenitally. If left untreated, the disease can ultimately lead to the degeneration of bones, heart, nerve tissue and other organs or tissues.

Little is known about the molecular biology of *Treponema pallidum* and less about the mechanisms of DNA synthesis and repair in this spirochete. The *T. pallidum* organism has an extremely long generation time (generally estimated at around 30 hours), but the limitations on its growth rate are unknown (1). It was hypothesized some 20 years ago from fragmentary data on the rate of DNA synthesis in a suboptimal in vitro culture system, that DNA synthesis is very slow in *T. pallidum* (2). DNA repair in *T. pallidum* appears to be defective with regard to oxidative lesions (3), but little else is known. This is unfortunate, since defects in DNA repair may relate to the fact that this treponeme cannot be grown in a cell free system, or be maintained at present even in the presence of tissue culture cells (4). Therefore, the isolation of the gene for DNA polymerase I from *T. pallidum* could be very important in answering questions about DNA replication and repair since it is important in both of these essential functions.

The DNA polymerase I enzyme, in general, is known to be involved in several important pathways of DNA repair and gap filling on the lagging strand during DNA replication (5). The gene has been found in all bacteria examined with the exception of a few species of Mycoplasmas and Archaebacteria (6,7). In most organisms, the enzyme contains three distinct domains: a 5'–3' exonuclease (important in removing damaged strands of DNA repair and removing RNA primers in replication); a 3'–5' exonuclease (which proofreads the DNA resulting from polymerization by the enzyme itself); and the polymerase domain, organized in this order from amino to carboxyl terminus of the protein (5). Because of the three domain structure, these enzymes are very large. The proofreading domain appears to be missing from the DNA polymerase I enzymes from *Thermus aquaticus*, *Mycobacterium tuberculosis*, and *Mycobacterium leprae* (8,9,10). The polymerase domain is highly conserved in all of the sequenced genes. There is more variability in the other domains, but specific amino acid motifs are found (11).

Due to the lack of a feasible system for growing *T. pallidum* in a clinical setting (*T. pallidum* can only be grown in tissue culture and cannot be serially passaged (4)), clinical diagnosis has traditionally depended on serological testing for antibody against *T. pallidum* (13). Direct testing for the presence of *T. pallidum* has been largely limited to darkfield examination of the primary chancre for the presence of spirochetes having the morphology of *T. pallidum* (13). This test lacks sensitivity and requires personnel training and experience to achieve accurate results. Consequently, this has led to the search for a PCR based test which should be highly sensitive and, with the choice of the proper target, could be very specific.

Orle et al. have reported the use of a PCR based test for the detection of syphilis (14). The specificity of this test is dependent on the choice of primers. In addition, U.S. Pat. Nos. 4,868,118; 5,350,842; and 5,508,168 describe a PCR based technique for clinical detection of *T. pallidum*. All of these patents involve the use of the 47 kD major immunogen, which is believed to be a carboxypeptidase involved in cell wall synthesis, and is further a penicillin binding protein (PBP) (19). Although this protein shows some cross-reactivity both immunologically and by PCR, it has no clear homologues by DNA sequence. This can be a major difficulty in cases of cross-reactivity since primers can only be selected for PCR by trial and error, i.e. known conserved and variant sequences are not known. This problem is inherent in all of the PCR based tests for *T. pallidum* described above. In no case does the gene used have clear homologues among known proteins. This is due to the fact that all of these genes were cloned after being identified as targets for an antibody response from the human host, none were cloned on the basis of function.

Therefore, there is a need for sensitive, specific methods for the detection of *T. pallidum*. Such methods would be particularly useful for facilitating a clinical diagnosis of syphilis. In addition, there is a need for probes and primers specific for *T. pallidum* to be used in detection methods and as scientific research tools to investigate the *T. pallidum* organism and to develop therapies and treatments.

SUMMARY OF THE INVENTION

Nucleic acid and amino acid sequences of the DNA polymerase I region of the *Treponema pallidum* genome and sequences of nucleic acid molecules that selectively hybridize with nucleic acid molecules encoding the DNA polymerase I enzyme from *Treponema pallidum* or complementary sequences thereof are described herein. The nucleic acid molecules are useful for the production of recombinant DNA polymerase I enzyme or as probes to detect the presence of *T. pallidum* in a sample or specimen with high sensitivity and specificity. The nucleic acid and amino acid sequences are also useful as laboratory research tools to study the organism and the disease and to develop therapies and treatments for syphilis.

Nucleic acids molecules for detecting *Treponema pallidum* are identified herein. In particular, nucleic acid molecules are described that are specific for unique regions of the nucleic acid molecule encoding the organism's DNA polymerase I. Antibodies specific for unique regions of the organism's DNA polymerase can be generated that are useful for detecting *T. pallidum* in a sample or for further isolation of the DNA polymerase I enzyme by techniques such as affinity chromatography. Isolated, recombinant, and synthetic DNA polymerase I from *T. pallidum*, methods of making the same, and methods for the use thereof are also described.

Therefore, it is an object of the invention to provide improved materials and methods for detecting and differentiating *Treponema pallidum* organisms in clinical and laboratory settings.

It is a further object of the invention to provide nucleic acid probes and primers specific for *T. pallidum*.

It is a further object of the invention to provide nucleic acid probes specific for the DNA polymerase I gene of *T. pallidum*.

It is a further object of the invention to provide an isolated DNA polymerase enzyme of *T. pallidum*.

It is a further object of the invention to provide antibodies specific for the DNA polymerase enzyme of *T. pallidum*.

It is a further object of the invention to provide methods for detecting, diagnosing, or monitoring the progress of therapy for syphilis that are sensitive and specific for *T. pallidum*.

These and other objects, features, and advantages of the present invention will become apparent after a review of the following detailed description of the disclosed embodiments and the appended claims.

BRIEF DESCRIPTION OF THE DRAWINGS

FIG. 1 is the primary amino acid sequence of DNA polymerase I from *T. pallidum* as deduced from the DNA sequence of the gene (PolA) and corresponds to SEQ ID NO: 8. Sequences lacking homology to the gene from *E. coli* (including the two insert regions) are underlined. Sequences used to generate primers for PCR are in bold.

FIG. 2 is a schematic representation of the sequencing strategy used to generate the complete sequence of the PolA gene and surrounding DNA. Sequences generated from the PstI and ClaI clones are indicated using the base pair count of the sequence set forth in FIG. 1. Areas designated as boxes 1 and 2 were sequenced by chromosome walking using a partial digest of the treponemal chromosome with the enzyme Sau3A.

FIG. 3 lists the DNA sequences of the four specific primers indicated in the amino acid sequence of FIG. 1 and correspond to SEQ ID NOS: 4–7. Primer pairs 1 and 2 are used together as are primer pairs 3 and 4. Each set generates an amplicon of approximately 370 base pairs.

DETAILED DESCRIPTION OF THE DISCLOSED EMBODIMENTS

Nucleic acid and amino acid sequences of the DNA polymerase I region of the *Treponema pallidum* genome are provided herein. The nucleic acid, or nucleotide, sequence of the coding region of DNA polymerase I gene (PolA) of *T. pallidum* is set forth as SEQ ID NO: 1. The amino acid sequence of the PolA gene product of *T. pallidum* is set forth as SEQ ID NO: 8. Also provided herein are sequences of nucleic acid molecules that selectively hybridize with nucleic acid molecules encoding the DNA polymerase I enzyme from *Treponema pallidum*. The nucleic acid molecules described herein are useful for the production of recombinant DNA polymerase I enzyme or as probes to detect *T. pallidum* in a sample or specimen with high sensitivity and specificity. The probes can be used to detect the presence of *T. pallidum* in the sample, diagnose infection with the disease, quantify the amount of *T. pallidum* in the sample, or monitor the progress of therapies used to treat the infection. The nucleic acid and amino acid sequences are also useful as laboratory research tools to study the organism and the disease and to develop therapies and treatments for the disease.

The gene encoding a functional DNA polymerase I from *Treponema pallidum*, provided as SEQ ID NO: 1, may be inserted into a vector and recombinantly expressed in a living organism to produce the recombinant DNA polymerase I enzyme. Alternatively, the DNA polymerase I enzyme of *T. pallidum* can be synthesized using the amino acid sequence provided as SEQ ID NO: 8. The isolated, recombinant or synthetic DNA polymerase I enzyme from *T. pallidum*, or fragments thereof, can be administered to animals to produce antigens for the production of antibodies useful for the specific detection of *T. pallidum*. Antibodies to the enzyme may also be used in production facilities or laboratories to isolate additional quantities of the enzyme, such as by affinity chromatography. It will be understood by those skilled in the art that minor amino acid substitutions or deletions may be present in a functional DNA polymerase I, or fragment thereof.

*T. pallidum* Probes

As shown in FIG. 1, the underlined amino acid sequences lacking homology to the amino acid sequence of the DNA polymerase I enzyme of *E. coli* provide corresponding nucleic acid sequences (SEQ ID NOs 2 and 3) which may be used as probes to detect *T. pallidum*. Examples of two particularly useful probes are provided in SEQ ID NOs: 6 and 7. These probes can be used to selectively hybridize with samples containing nucleic acid molecules of *T. pallidum*. Detection can be facilitated by means such as the polymerase chain reaction or ligase chain reaction, for example. Alternatively, the probe is labelled with a detectable label and detected in accordance with methods well known to those skilled in the art.

It will be understood by those skilled in the art that additional probes may be derived without undue experimentation from the sequence provided in SEQ ID NO:1, or complementary sequences thereof, which hybridize with specificity to *T. pallidum*. Therefore, the probes shown in SEQ ID NOS: 4–7 are only provided as examples of probes specific for *T. pallidum* that can be derived from SEQ ID NO:1. The gene for DNA polymerase I for *T. pallidum* offers a number of very unusual sequences for use as PCR primers. The PolA gene is well characterized from a number of different bacterial species, including X-ray crystallographic data on the protein's structure from the Klenow fragment of *E. coli* (18). Therefore, comparisons can be made between the *T. pallidum* PolA gene sequence and the PolA gene sequence from other organisms to identify unique or non-homologous regions that would be useful to construct probes that would be specific for *T. pallidum* and have minimal cross-hybridization with the PolA gene from other organisms. One useful computer program for generating selective probes from SEQ ID NO:1 is the Gene Jockey program available from Biosoft (Cambridge, UK).

The term "isolated" in the context of a compound, such as a protein, nucleic acid or antibody, is defined herein as free from at least some of the components with which the compound naturally occurs. A nucleic acid which "selectively hybridizes" is defined herein as a nucleic acid which hybridizes to a portion of a *Treponema pallidum* DNA polymerase I gene, and which does not hybridize with other nucleic acids so as to prevent determination of adequate positive hybridization to a portion of a *Treponema pallidum* DNA polymerase I gene. Therefore, in the design of hybridizing nucleic acids, selectivity will depend upon the other components present in a sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus, has the same meaning as "specifically hybridizes". The selectively hybridizing nucleic acids of the invention can have at least 70%, 80%, 85%, 90%, 95%, 97%, 98%, and 99% complementarity with the segment of the sequence to which it hybridizes.

The invention contemplates sequences, probes, and primers that selectively hybridize to the encoding DNA or the complementary, or opposite, strand of DNA as those specifically provided herein. Specific hybridization with nucleic acid can occur with minor modifications or substitutions in the nucleic acid, so long as functional species-specific hybridization capability is maintained. The term "probe" is defined herein to include nucleic acid sequences that can be used as probes or primers for selective hybridization with complementary nucleic acid sequences for their detection or amplification. Such probes can vary in length from about 5 to 100 nucleotides, or preferably from about 10 to 50 nucleotides, or most preferably about 18–24 nucleotides. Therefore, the terms "probe" or "probes" as used herein are defined to include primers. Isolated nucleic acids are provided herein that selectively hybridize with the species-specific nucleic acids under stringent conditions and should have at least 5 nucleotides complementary to the sequence of interest. See generally, Sambrook (12).

If used as primers, the invention also preferably provides compositions including at least two nucleic acids which hybridize with different regions so as to amplify a desired region. Depending on the length of the probe or primer, the target region can range between 70% complementary bases and full complementarity and still hybridize under stringent conditions. For example, when diagnosing the presence of the *Treponema pallidum*, the degree of complementarity between the hybridizing nucleic acid (probe or primer) and the sequence to which it hybridizes (e.g., *T. pallidum* DNA from a sample) is at least enough to distinguish hybridization with a nucleic acid from other yeasts and filamentous fungi. Examples of nucleic acids unique to *T. pallidum* are provided in the listed sequences so that the degree of complementarity required to distinguish selectively hybridizing from nonselectively hybridizing nucleic acids under stringent conditions can be clearly determined for each nucleic acid.

Methods for the Detection and Identification of *T. pallidum*

Methods of using the nucleic acids described herein to detect and identify the presence of *T. pallidum* are also provided. The method involves the steps of obtaining a sample suspected of containing *T. pallidum*. The sample may be taken from an individual, such as a primary chancre, blood, saliva, vaginal mucosa, tissues, etc., or taken from the environment. The *T. pallidum* cells can then be lysed, and the DNA extracted and precipitated. The DNA is preferably amplified using primers derived from the DNA polymerase I region of the *T. pallidum* rDNA. Examples of such primers are shown below as SEQ ID NOS: 4–7. Detection of *T. pallidum* DNA is achieved by hybridizing the amplified DNA with a *T. pallidum* species-specific probe that selectively hybridizes with the DNA. Detection of hybridization is indicative of the presence of *Treponema pallidum*.

Preferably, detection of nucleic acid hybridization with probes can be facilitated by the use of detectable moieties. For example, the probes can be labeled with biotin and used in a streptavidin-coated microtiter plate assay. Other detectable moieties include radioactive labeling, enzyme labeling, and fluorescent labeling, for example.

*T. pallidum* Detection Kit

The invention further contemplates a kit containing one or more *Treponema pallidum* DNA polymerase I specific nucleic acid probes that can be used for the detection of *T. pallidum* organisms in a sample. Such a kit can also contain the appropriate reagents for hybridizing the probe to the sample and detecting bound probe. The invention further contemplates a kit containing one or more *T. pallidum* DNA polymerase I specific antibodies that can be used for the detection of *T. pallidum* organisms in a sample.

Modifications to the PolA Gene

Altered sequences can be used in accordance with the present invention which include deletions, additions or substitutions of different residues resulting in a sequence that encodes the same or a functionally equivalent gene product. The gene product itself may contain deletions, additions, or substitutions of amino acid residues within a DNA polymerase I sequence that result in a silent change, thus producing a functionally equivalent DNA polymerase I protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine, and arginine; amino acids with uncharged polar head groups having similar hydrophilicity values include the following: glycine, asparagine, glutamine, serine, threonine, and tyrosine; and amino acids with nonpolar head groups include alanine, valine, isoleucine, leucine, phenylalanine, proline, methionine, and tryptophan.

The nucleotide sequences described herein can be engineered to alter a DNA polymerase I coding sequence to produce a variety of results, including but not limited to, alterations which modify processing and expression of the gene product. For example, mutations may be introduced using techniques which are well known in the art, such as site-directed mutagenesis, to insert new restriction sites, to alter glycosylation patterns, phosphorylation, and the like.

In addition, a conserved DNA polymerase I region or a modified DNA polymerase I sequence may be ligated to a heterologous sequence to encode a fusion protein. For example, when screening peptide libraries for molecules that bind DNA polymerase I enzymes, it may be useful to encode a chimeric DNA polymerase I protein expressing a heterologous epitope that is recognized by a commercially available antibody. A fusion protein may also be engineered to contain a cleavage site located between a DNA polymerase I sequence and the heterologous protein sequence, so that the DNA polymerase I may be cleaved away from the heterologous moiety.

Production of Synthetic or Recombinant DNA Polymerase I

Furthermore, the coding sequence of DNA polymerase I could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letter* 21:719; and Chow and Kempe, 1981, *Nuc. Acids Res.* 9(12):2807–2817. Alternatively, the protein itself could be produced using chemical methods to synthesize a DNA polymerase I amino acid sequence in whole or in part. For example, peptides can be synthesized by solid phase techniques, cleaved from the resin, and purified by preparative high performance liquid chromatography (e.g., see Creighton, 1983, *Proteins Structures And Molecular Principles*, W. H. Freeman and Co., N.Y. pp. 50–60). The composition of the synthetic peptides may be confirmed by amino acid analysis or sequence (e.g., the Edman degradation procedure; see Creighton, 1983, *Proteins, Structures and Molecular Principles*, W. H. Freeman and Co., N.Y., pp. 34–49).

In order to express a biologically functional or active DNA polymerase I, or conserved DNA polymerase I region, the nucleotide sequence coding for DNA polymerase I, or a homologue or functional equivalent, can be used directly as a probe for the detection of hybridizing nucleic acids in a sample or individual, or be inserted into an appropriate expression vector, i.e., a vector which contains the necessary elements for the transcription and translation of the inserted coding sequence. The DNA polymerase I gene products, as well as host cells or cell lines transfected or transformed with recombinant DNA polymerase I expression vectors, can be used for a variety of purposes. These include but are not limited to generating antibodies (i.e., monoclonal or polyclonal) that competitively inhibit activity of DNA polymerase I protein and neutralize its activity; and antibodies that mimic the activity of DNA polymerase I binding partners such as a receptor. Anti-DNA polymerase I antibodies may be used in detecting and quantifying expression of DNA polymerase I levels in cells and tissues, as well as isolating DNA polymerase I-positive cells.

Characteristics of the *T. pallidum*. PolA Gene

The gene described herein offers several advantages over previous genes that have been used for PCR identification of *Treponema pallidum*. One of the most important characteristic is that the gene described herein is a gene for a known protein. Genes for DNA polymerase I have been sequenced from a number of different sources, and some are well characterized. The PolA gene from *T. pallidum* contains numerous sequences that are not found in characterized genes, and at least the one set of primers tested is apparently not present in other spirochetes in which the DNA polymerase I genes have not been characterized. Therefore, the gene described herein makes an ideal target for PCR or probe applications, since it is a highly conserved and essential gene with unique sequences can be used for the development of specific primers for PCR or probes for probe based technology.

Other primers used for the identification of *T. pallidum* by PCR have been based on genes cloned for antigenic reactivity. None of these genes are well characterized in the sense that analogs from other bacteria are known. The best biochemically characterized of these genes and their proteins are known to show some cross-reactivity with other bacteria, but construction of primers or probes is limited to empirical testing since sequences that are specific to *T. pallidum* cannot be identified if the analogs are unknown from other bacteria. Because the PolA gene contains numerous sequences that appear to be unique to *T. pallidum*, greater flexibility in allowed in the construction of clinical primers and probes. This should greatly improve the application of PCR in the clinical setting for *T. pallidum*. Preliminary testing indicates that, when used for PCR, the PolA gene primers are at least as sensitive as the primers presently available.

As described above, the sequence for the PolA gene from *T. pallidum* has several unusual characteristics. These characteristics are useful for PCR applications and *T. pallidum* detection. The DNA polymerase enzyme encoded by the gene also has novel properties relating to its mode of polymerization.

PolA Gene Sequence Strategy

The sequence of the gene was reconstructed from two overlapping clones (from a ClaI and PstI library of *T. pallidum* genomic DNA) supplemented by chromosome walking to complete the sequence. FIG. 2 shows the sequencing strategy used in completing the sequence. The complete sequence of the gene for DNA polymerase I as well as the part of an upstream coding for the carboxyl terminus of the enzyme 5'-nucleotidase is given in SEQ ID NO: 9. The *T. pallidum* PolA gene codes for the largest known DNA polymerase I (997 codons long). The predicted protein (SEQ ID NO: 8) is 112 kD in size. The protein contains motifs for all three of the enzymatic activities of DNA polymerase I, but has several novel characteristics not found in any of the ten or so other PolA gene sequences presently available.

First of all, the amino acid sequence contains two large inserts not found in other PolA genes which code for inserts of 32 and 34 amino acids respectively. The first of these inserts is at the junction of the 5'–3' endonuclease with the 3'–5' endonuclease, and the second is inside the 3'–5' endonuclease. The effects these two inserts on the two exonuclease activities are not known. The second unusual characteristic is an extremely high cysteine content which could render the enzyme oxygen labile. The enzyme contains 24 cysteine residues; the other sequenced DNA polymerase I enzymes from bacteria all contain only one to three cysteines by comparison. The cysteines are found predominately in the nonconserved areas, but are common throughout the two exonuclease domains. They are very uncommon in the highly conserved polymerase domain. These two unusual characteristics are of interest in terms of two areas of potential applications to molecular biology beyond their importance in terms of understanding the biology and pathogenesis of this microorganism. Each of these areas of potential application to clinical microbiology is discussed below.

With the two inserts (one of which interrupts the 3'–5' endonuclease), it is quite possible that the *T. pallidum* PolA enzyme may have unique features which could make it useful as a molecular biology reagent. The gene can be cloned by PCR amplification (with the introduction of synthetic restriction sites flanking the gene) followed by ligation into the plasmid pUC8, for example. The gene can be subcloned into an expression vector where expression can be controlled since the gene may prove lethal in *E. coli*. PolA genes are commonly lethal on high copy number plasmids. Even the *E. coli* PolA enzyme was originally cloned on a low copy number plasmid because of this property (12).

The unique areas of the enzyme, particularly the inserts described above, may affect the function of the enzyme and its ability to proofread. One of these inserts is contained in the proofreading exonuclease and may effect the activity of the enzyme. The sensitivity of the enzyme to oxygen due to the very high cysteine content predicted from the gene sequence can be quantified. Therefore, the enzyme may be a target for oxygen inactivation, which may explain the high sensitivity of this spirochete for oxygen even though it seems to be capable of respiration.

The problems unsolved by the prior art can be addressed with the PolA gene described herein because it codes for a protein that is well characterized in other systems and has at least ten other known sequences in the GenBank database to which it can directly be compared. This data base will certainly expand in the near future, including sequences from other spirochetes. PolA genes are highly conserved within a species (exhibiting essentially no variation) and are not dispensable, and thus, should be found in all strains of a particular species. For example, the DNA polymerase gene for herpesviruses is highly conserved (20). The unique segments of the sequence discussed above should provide *T. pallidum*-specific primers for PCR. Examples for PCR of the unique areas of the gene are discussed below.

The *T. pallidum* PolA gene codes for a protein with a number of amino acid sequences not seen in other DNA polymerase I enzymes. FIG. 1 shows the amino acid sequence with the unique inserts underlined. Cysteine is one of the rarest amino acids in the vast majority of proteins, and only zero to three residues have been found in DNA polymerase I proteins with a known DNA sequence to date. The function of these unique areas and their effect on the activity of the enzyme are not yet known, but their potential for use in PCR is great. For example, the two unique inserts indicated in FIG. 1 were used to search the GenBank data base; no sequences of high identity were found, and no homology to any regions of the sequenced PolA genes was seen.

Preliminary work with one set of primers taken from two of the high cysteine sequences (primers and location in sequence shown in FIG. 1 and SEQ ID NOS: 6–7) indicate that these sequences are not found in *Borrelia burgdorferi*, *Treponema phagedenis*, *Treponema denticola*, or *Leptospira interrogans*. On the other hand, besides the Nichols strain of *T. pallidum*, one strain of *T. pallidum* subspecies pertenue and a recently isolated street strain of *T. pallidum* subspecies pallidum were tested, and both were positive for these sequences. Thus, both sequences appear to be highly conserved in *T. pallidum* but completely unique when compared to related spirochetes.

Because the PolA gene is important for bacterial survival (5), it is found in all strains of a particular species. Therefore, it is unlike some genes which code for surface proteins, and its clinical utility should only be dictated by sensitivity and specificity. This conservation in all strains allows for unambiguous proof of the presence of *T. pallidum* in questionable cases such as the purposed presence of *T. pallidum* in gum disease (21).

Computer analysis and GenBank Accession Number

The sequence for the PolA gene and surrounding DNA has been assigned the GenBank accession number TPU57757. Comparisons to known gene sequences were made using the GCG (Genetics Computer Group) package from the University of Wisconsin and the MacVector software package of Eastman Kodak.

The invention may be further demonstrated by the following non-limiting examples.

EXAMPLE 1

Cloning and Sequencing of the PolA Gene from *T. pallidum*.

The PolA gene was originally discovered as a partial sequence on a recombinant designated Tp 615 during immunological screening of a ClaI library of *T. pallidum* DNA. This recombinant contained 537 codons of the PolA gene, but also contained a piece of noncontiguous DNA. A second recombinant from a PstI library and chromosomal "walking" was used to generate the complete sequence. The recombinant from the PstI library was found using an oligonucleotide probe from the sequence derived from Tp 615. To perform the chromosomal "walking", in accordance with the strategy shown in FIG. 2, treponemal DNA was partially digested with Sau3A and the resulting fragments were ligated into the BamHI site of pUC8. Sequencing was then performed using a specific primer derived from the known sequence of the gene and primers specific for the M13 sites used in sequencing in the pUC8 plasmid.

DNA sequencing was performed both by manual and automatic methods. A final total of approximately 3.9 Kb of *T. pallidum* chromosomal DNA were sequenced containing the total PolA gene and 100 codons of the gene immediately on the 5' side of the PolA gene (a putative 5'-nucleotidase gene). Manual sequencing was performed by the method of Sanger et al (22) using the United States Biochemical (USB) sequencing kit with a-S35 dATP and Sequenase 2.0 as the polymerase. Automated DNA sequencing was carried out using the ABI PRISM Dye Terminator cycle sequencing Core Kit with ampliTaq DNA polymerase. DNA templates were purified with the Qiagen Plasmid Kit; PCR fragments were purified with the Qiaquick PCR purification kit (Qiagen Inc., Chatsworth, Calif.). Automated sequencing runs were run on 6% polyacrylamide gels in an ABI 370A sequencer.

The PolA gene was cloned from *T. pallidum* genomic DNA by PCR amplification once the sequence of the gene and surrounding DNA had been determined. PCR primers were synthesized approximately 50 bp beyond the gene both on the 5' and 3' sides of the reading frame. The 5' primer was as follows: CCC GAATTCTGTGCCAATCTGCTTTTCCGG. (SEQ ID NO: 10) The underlined EcoRI sequence was not present in the gene and was introduced for cloning purposes. Likewise, on the 3' side of the gene a synthetic HindIII site was introduced for cloning purposes; the sequence of this primer was as follows: TGAA AAGCTTGGTAACCTCATAACGTGCCCT (SEQ ID NO: 11) with the artificial HindIII site underlined. After a 30 cycle amplification, the PCR product was purified and cut with EcoRI and HindIII and the resulting fragment with restricted ends was ligated into an appropriately cut pUC8 plasmid. Colonies containing the 3150 bp insert were identified as β-galactosidase negative colonies; the insert size was determined by gel electrophoresis of plasmid minipreps. Recombinants containing inserts of the appropriate size were picked and resequenced to confirm the previously determined sequence of the gene. The entire sequence is shown in SEQ ID NO: 9, and the sequence corresponding to the gene for DNA polymerase I is shown in SEQ ID NO: 1.

EXAMPLE 2

Expression of the PolA Gene Product from *T. pallidum*

The technique described above in Example 1 was used to clone the PolA gene into the ProEX™ HT expression vector with the following modification: the 5' end of the gene began directly after the artificial restriction site which put it in frame with the β-galactosidase gene promoter of the plasmid. This particular plasmid was picked both for ease of purification of the protein product (because of the synthetic polyhistidine leader) and for the fact that expression can be controlled. This was of interest because it was not known whether the DNA polymerase I protein from *T. pallidum* might be toxic for the host *E. coli*. After induction of expression of the gene with 0.6 mM isopropyl-β-D-thiogalactopyranoside (IPTG), whole cell lysates of stationary phase cells were prepared, and the whole cell proteins were separated by SDS-PAGE on 10% polyacrylamide gels. Proteins were transferred from the gel to nylon membranes using the method of Towbin et al. (23), and the PolA gene product was detected with a commercial antibody against the N-terminal polyhistidine leader of the expression vector. Using this technique, a recombinant plasmid was constructed starting at nucleotide 605 (at the putative ATG starting codon).

EXAMPLE 3

Detection of PolA Gene Product by Immunological Means and Determination of the Amino Terminus of the Protein The putative DNA polymerase I from *T. pallidum* was detected from *E. coli* harboring the expression vector as indicated in Example 2 with a commercial antibody against the polyhistidine leader of the protein. This antibody was used as the control for locating the protein when tested with antibodies raised against specific peptides whose sequences were derived from the predicted sequence of the protein. The specific peptides and their position within the predicted DNA polymerase I sequence are given in Table 1 below.

TABLE 1
Synthetic Peptides and Their Position in the Sequence of the DNA Polymerase I from *Treponema pallidum*.
Seq88 (Amino Acids 292–311) Q-E-I-D-T-E-A-T-N-D-T-L-Q-M-T-E-S-S-V-L (SEQ ID NO: 12)
Seq89 (Amino Acids 323–342) S-Q-V-E-G-R-A-S-T-P-E-V-N-S-V-L-K-S-E-L (SEQ ID NO: 13)
Seq90(Amino Acids 337–356) V-L-K-S-E-L-K-T-S-A-V-S-G-A-I-P-I-E-N-R (SEQ ID NO: 14)

The first three peptides were internal and were chosen from unique sequences in the protein which have not been found in any of the DNA polymerase I enzymes whose sequence is presently known. Thus, antibodies against these peptides should react with the treponemal polymerase but not with the DNA polymerase I from *E. coli*. The fourth peptide was derived from an alternate GTG start codon which would add 18 amino acids onto the length of the enzyme (GTG amino terminus peptide). The first three peptides were synthesized with a carboxyl terminal cysteine and were coupled through this cysteine to bovine serum albumin (BSA) and to keyhole limped hemocyanin (KLH). The fourth peptide (GTG amino terminus peptide) was very hydrophobic and was not coupled to a carrier protein but directly solubilized with dimethyl sulfoxide (DMSO). The conjugated peptides (or DMSO solubilized) were then mixed 50:50 with Hunter's Titermax adjuvant and injected into rabbits (100 mg per rabbit). The rabbits were boosted with the same amount at 3–4 weeks later. Rabbits were bled before injection, at boosting, and six weeks post initial injection and the serum was collected.

DISCUSSION AND SUMMARY OF EXPERIMENTAL RESULTS

The clone (designated Tp 615) was originally discovered during immunological screening of a library of *T. pallidum* DNA generated by digestion of isolated treponemal DNA with the restriction enzyme ClaI. The clone proved to be a chimera containing DNA from two different locations in the treponemal genome and with approximately 50% of the PolA gene present (537 codons). A second library of treponemal DNA, constructed by PstI digestion of *T. pallidum* DNA contained a further 300 codons. The final complete sequence was constructed by chromosomal walking, as described above. The complete strategy for sequencing of the gene and the location of PolA and the upstream gene are shown in FIG. 2.

A total of 3885 bp were sequenced containing the complete PolA gene and the terminal 100 codons of an upstream gene which had strong sequence homology to a putative 5'-nucleotidase gene of *Haemophilis influenzae* (24), an enzyme involved in scavenging of nucleotide bases from the environment (25). The complete sequence of the PolA gene showed a number of unusual characteristics not found in other bacterial PolA genes. The first was the high cysteine content. The second was the presence of two large inserts in the exonuclease domains that had no sequence homology to known DNA polymerase I enzymes. These sequences are indicated in FIG. 1. These inserts accounted for the large size of the DNA polymerase I compared to others that have been sequenced since the other homologous areas of the enzyme were fairly similar in size to known DNA polymerase I enzymes.

The known sequence of the gene and surrounding DNA was used to clone the entire gene by PCR. The amplification primers contained synthetic restriction sites for insertion into the target plasmid. This method was initially used to clone the gene into the plasmid pUC8. It gave rise to a recombinant plasmid with a 3150 bp insert as expected. This recombinant was completely resequenced to confirm the initially determined sequence. Complementation assays with a polA-mutant of *E. coli* and Western blot assay indicated little if any protein was being produced by this recombinant. Because of these results, the same method was used to produce an amplicon that was inserted into the ProEX™ HT expression vector giving rise to a 6 Kb recombinant plasmid containing the complete PolA gene in frame with the β-galactosidase promoter found in the plasmid. Induction with IPTG resulted in the production of a protein product of the expected size (113 kD).

The first unique feature of the primary amino acid sequence was the unusually high content of the amino acid cysteine. In *Escherichia coli* proteins, cysteine is the rarest of all of the amino acids (26). This amino acid is extremely rare in all other DNA polymerase I genes (polA) that have been sequenced. They all contain only 0–3 residues of the amino acid. In contrast, the *T. pallidum* gene coded for 24 cysteines. The cysteine content, which comes to approximately 2.4% of the total amino acids, is extremely high for intracellular proteins of bacteria (27, 28).

This high cysteine content suggests two possibilities: that the enzyme may have added or lost functions found in the other enzymes of this class, and that the protein may prove highly sensitive to inactivation by molecular oxygen. If the protein is highly sensitive to oxidative inactivation, it would provide a major reason for the poor DNA repair seen from damage caused by hydrogen peroxide (29). Since this enzyme is involved in gap filling, both in DNA repair and replication (it is involved in filling the gaps and removing RNA primers on the lagging strand during replication), an unusual sensitivity to oxygen inactivation would sensitize *T. pallidum* to this form of damage. It would also suggest a reason for the high requirement for sulfhydryl compounds in *T. pallidum* (30) as they would be necessary to keep the redox potential low enough to keep DNA polymerase I in a sufficiently reduced state to function.

Several other treponemal enzymes which we have sequenced [a putative alanine racemase (GenBank Accession Number TPU57756) and a homolog of either octaprenyl- or hexaprenyl pyrophosphate synthetase (GenBank Accession Number TPU95214)] as well as several enzymes sequenced by others also appear to be high in cysteine, which would support this contention for the sensitivity of T. pallidum to oxygen. Although this phenomenon is not universal in treponemal proteins, it does suggest the possibility that T. pallidum has a number of key enzymes which would be abnormally sensitive to oxygen inactivation.

The second unique feature was the insertion of two sequences into the protein (both approximately 35 amino acids long) which show no homology to any area in other DNA polymerase I enzymes. These two insertions were found at the junction of the two exonuclease domains and inside the 3'–5' exonuclease domain. The two insertions account for most of the added length of this protein which is the largest PolA gene sequenced to date. These two inserts and the high cysteine content were of especial interest to us since they present many areas of unique sequence which could be used in a PCR based test for the identification of T. pallidum.

Expression of the gene product in the fusion protein was low. This may have been due to the exceptionally high use of "rare" codons for *E. coli* in the gene (31). Many of the most rarely used codons in *E. coli* were plentiful in this gene. For example, the AGA and AGG codons which are the most infrequently used codons in *E. coli* (both code for arginine) made up 25% of the arginine codons in this gene (17/68), which is approximately six times the rate of usage expected in *E. coli* (31). These two codons are common in a number of other genes sequenced from *T. pallidum* (data not shown) and indicate codon usage may be quite different in *T. pallidum* when compared to *E. coli*. Several other "rare" codons were used in disproportionate amounts. Besides the effects on expression in *E. coli*, they may also indicate low level expression of this gene in *T. pallidum.*

It should be understood that the foregoing relates only to preferred embodiments of the present invention, and that numerous modifications or alterations may be made therein without departing from the spirit and the scope of the invention as set forth in the appended claims.

References

All of the references cited in this Specification are hereby incorporated by reference in their entireties, including the following.

1. Cumberland, M. C. and T. B. Turner. 1949. The rate of multiplication of *Treponema pallidum* in normal and immune rabbits. *Am. J. Syphilis Gonorr. Ven. Dis.* 33, 201–212.
2. Baseman, J. B., J. C. Nichols, and S. Mogerley. 1979. Capacity of virulent *Treponema pallidum* (Nichols) for deoxyribonucleic acid synthesis. *Infect. Immun*. 23, 392–397.
3. Steiner, B. M., G. H. W. Wong, P. Sutrave, and S. Graves. 1984. Oxygen toxicity in *Treponema pallidum*: deoxyribonucleic acid single-stranded breakage induced by low doses of hydrogen peroxide. *Can. J. Microbiol.* 30, 1467–1476.
4. Fieldsteel, A. H., D. L. Cox, and R. A. Moeckli. 1981. Cultivation of virulent *Treponema pallidum* in tissue culture. *Infect. Immun*. 32, 908–915.
5. Kornberg, A., and T. A. Baker. 1992. DNA replication, 2nd edition. W. H. Freeman & Co., New York.
6. Dybvig, K. and L. L. Voelker. 1996. Molecular biology of Mycoplasmas. *Ann. Rev. Microbiol.* 50, 25–57.
7. Built, C. J. et al. 1996. Complete genome sequence of the methanogenic archaeon, *Methanococcus jannaschii. Science* 273, 1058–1073.
8. Lawyer, F. C., S. Stoffel, R. K. Saiki, K. Myambo, R. Drummond, and D. H. Gelfand. 1989. Isolation, Characterization, and expression in *Escherichia coli* of the DNA polymerase gene from Thermus aquaticus. *J. Biol. Chem*. 264, 6427–6437.
9. Huberts, P. and V. Mizrahi. 1995. Cloning and sequence analysis of the gene encoding the DNA polymerase I from *Mycobacterium tuberculosis. Gene* 164, 133–136.
10. Fsihi, H. and S. T. Cole (1995) The *Mycobacterium leprae* genome: systematic sequence analysis identifies key catabolic enzymes, ATP-dependent transport systems and a novel PolA locus associated with genomic variability. *Mol. Microbiol*. 16, 909–919.
11. Blanco, L., A. Bemad, M. A. Blasco, and M. Salas. 1991. A general structure for DNA-dependent DNA polymerase. *Gene* 100, 27–38.
12. Sambrook, J., E. F. Fritsch, and T. Maniatis. 1989. Molecular cloning: a laboratory manual, 2nd ed. Cold Spring Harbor Laboratory, Cold Spring Harbor, N.Y.
13. Larsen, S. A., B. M. Steiner, and A. H. Rudolph. 1995. Laboratory diagnosis and interpretation of tests for syphilis. *Clin. Microbiol. Rev*. 8, 1–21.
14. Orle, K. A., C. A. Gates, D. H. Martin, B. A. Body, and J. B. Weiss. 1996. Simultaneous PCR detection of *Haemophilus ducreyi, Treponema pallidum*, and Herpes Simplex Virus Types I and 2 from genital ulcers. *J. Clin. Microbiol*. 34, 49–54.
15. Grimprel, E., P. J. Sanchez, G. D. Wendel, J. M. Burstain, G. H. McCracken, Jr., J. D. Radolf, and M. V. Norgard. 1991. Use of polymerase chain reaction and rabbit infectivity testing to detect *Treponema pallidum* in amniotic fluid, fetal and neonatal sera, and cerebrospinal fluid. *J. Clin. Microbiol*. 29, 1711–1718.
16. Noordhoek, G. T., E. C. Wolters, M. E. J. De Jonge, and J. D. A . Embden. 1991. Detection by polymerase chain reaction of *Treponema pallidum* DNA in cerebrospinal fluid from neurosyphilis patients before and after antibiotic treatment. *J. Clin. Microbiol*. 29, 1976–1984.
17. Wicher, K., G. T. Noordhoek, F. Abbruscato, and V. Wicher. 1992. Detection of *Treponema pallidum* in early syphilis by DNA amplification. *J. Clin. Microbiol.* 30, 497–500.
18. Beese, L. S., V. Derbyshire, and T. A. Steitz. 1993. Structural of DNA polymerase I Klenow fragment bound to duplex DNA. *Science* 260, 352–355.
19. Weigel, L. M., J. D. Radolf, and M. V. Norgard 1994. The 47-kDa major lipoprotein immunogen of *Treponema pallidum* is a penicillin-binding protein with carboxypeptidase activity. *Proc. Natl. Acad. Sci. USA*, 91, 11611–11615.
20. Tenorio, A., J. E. Echevarria, I. Casas, J. M. Echevarria and E. Tabares. 1993. Detection and typing of human herpesviruses by multiplex polymerase chain reaction. J. Virolog. Methods 44, 261–269.
21. Riviere, G. R., M. A. Wagoner, S. A. Baker-Zander, K. S. Weisz, D. F. Adams, L. Simonson, and S. A. Lukehart. 1991. Identification of spirochetes related to *Treponema pallidum* in necrotizing ulcerative gingivitis and chronic periodontitis. *New England J. Med.* 325, 539–543.
22. Sanger, F. S., S. Nicklen, and A. R. Coulson. 1977. DNA sequencing with chain-terminating inhibitors. *Proc. Natl. Acad. Sci. USA* 74: 5463–5467.

23. Towbin, H., T. Stachelin, and J. Gordon. 1979. Electrophoretic transfer of proteins from polyacrylamide gels in nitrocellulose sheets: procedure and some applications. *Proc. Natl. Acad. Sci. USA* 76: 4350–4354.
24. Fleischmann, R. D., M. D. Adams, O. White, R. A. Clayton, E. F. Kirkness et al. 1995. Whole-genome sequencing and assembly of *Haemophilis influenzae*. *Science* 269: 496–512.
25. Zimmermann, H. 1992. 5'-nucleotidase: molecular structure and functional aspects. *Biochem. J*. 285: 345–365.
26. Wada, K., Y. Wada, F. Ishibashi, T. Gojobori, and T. Ikemura. 1992. Codon usage tabulated from the genebank genetic sequence data. *Nucleic Acid Res*. 20: 2111–2118.
27. Fahey, R. C., J. S. Hunt and C. C. Windham. 1977. On the cysteine and cystine content of proteins. *J. Mol. Evol*. 10: 155–160.
28. Thornton, J. M. 1981. Disulfide bridges in globular proteins. *J. Mol. Biol*. 151: 261–287.
29. Steiner, B. M., G. H. W. Wong, P. Sutrave, and S. Graves. 1984. Oxygen toxicity in *Treponema pallidum*: deoxyribonucleic acid single-stranded breakage induced by low doses of hydrogen peroxide. *Can. J. Microbiol*. 30: 1467–1476.
30. Fitzgerald. 1981. In vitro cultivation of *Treponema pallidum*: a review. *Bull. World Health Organ*. 59: 787–812.
31. Kane, J. F. 1995. Effects of rare codon clusters on high-level expression of heterologous proteins in *Escherichia coli*. *Curr. Opin. Biotechnol*. 6: 494–500.

We claim:

1. A nucleic acid probe for *Treponema pallidum*, wherein the probe selectively hybridizes with a nucleic acid molecule encoding the gene for *Treponema pallidum* DNA polymerase I, or a complementary sequence thereof, wherein the probe does not hybridize with other nucleic acid molecules so as to prevent a determination of adequate positive hybridization with the nucleic acid molecule encoding the gene for *Treponema pallidum* DNA polymerase I, or a complementary sequence thereof, and further wherein the probe is between 5 and 100 nucleotides in length.

2. The nucleic acid probe of claim 1, wherein the nucleic acid molecule encoding the gene for *Treponema pallidum* DNA polymerase I, comprises the sequence set forth in SEQ ID NO:1 or a complementary sequence thereof.

3. The nucleic acid probe of claim 1, having a nucleic acid sequence of SEQ ID NO:4, SEQ ID NO:5, SEQ ID NO:6, SEQ ID NO:7, or a complementary sequence thereof.

4. A method for detecting *Treponema pallidum* in a sample comprising combining the sample with a nucleic acid probe for *Treponema pallidum*, wherein the probe selectively hybridizes with a nucleic acid molecule encoding the gene for *Treponema pallidum* DNA polymerase I, or a complementary sequence thereof, the presence of hybridization indicating *Treponema pallidum* in the sample, wherein the probe does not hybridize with other nucleic acid molecules so as to prevent a determination of adequate positive hybridization with the nucleic acid molecule encoding the gene for *Treponema pallidum* DNA polymerase I, or a complementary sequence thereof, and further wherein the probe is between 5 and 100 nucleotides in length.

5. The method of claim 4, wherein the nucleic acid molecule encoding the gene for *Treponema pallidum* DNA polymerase I comprises the sequence set forth in SEQ ID NO:1 or a complementary sequence thereof.

6. The method of claim 4, wherein the nucleic acid probe has a nucleic acid sequence of SEQ ID NO:4, SEQ ID NO:5, SEQ ID NO:6, SEQ ID NO:7, or a complementary sequence thereof.

7. An isolated nucleic acid molecule encoding a *Treponema pallidum* DNA polymerase I enzyme.

8. An isolated nucleic acid molecule encoding a *Treponema pallidum* DNA polymerase I enzyme, wherein the nucleic acid molecule comprises the nucleotide sequence set forth in SEQ ID NO:1.

9. An isolated nucleic acid molecule encoding a *Treponema pallidum* DNA polymerase I enzyme, wherein the DNA polymerase I enzyme has the amino acid sequence set forth in SEQ ID NO:8.

10. Isolated DNA polymerase I enzyme from *Treponema pallidum*.

11. Isolated DNA polymerase I enzyme from *Treponema pallidum* comprising the amino acid sequence set forth in SEQ ID NO:8.

12. The DNA polymerase I enzyme of claim 10, wherein the enzyme is recombinant.

13. The DNA polymerase I enzyme of claim 10, wherein the enzyme is synthetic.

14. The nucleic acid probe of claim 1, wherein the probe selectively hybridizes with a portion of the *Treponema pallidum* DNA polymerase I gene provided in SEQ ID NOs: 2 or 3, or a complementary sequence thereof.

15. The nucleic acid probe of claim 14, wherein the probe is between 10 and 50 nucleotides in length.

16. The method of claim 4, wherein the probe selectively hybridizes with a portion of the *Treponema pallidum* DNA polymerase I gene provided in SEQ ID NOs: 2 or 3, or a complementary sequence thereof.

17. The nucleic acid probe of claim 16, wherein the probe is between 10 and 50 nucleotides in length.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 2991 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
ATGCAAGAGA AAAAAACGCT TTACCTTCTT GATGCCTACG GACTTATTTA TCGGAGTTAC          60

CACGCGTTCG CGCGTGCGCC GTTGATTAAC GACAGCGGTG CGAATGTTTC TGCCGTATAT         120

GGTTTTTTTC GGAGTTTGCA CACGCTCCTG TGTCACTATC GACCCCGTTA TTTTGTTGCT         180

GTTTTTGATT CTCTCACGCC TACCTTTCGG CACGTACAGT ACCCAGCCTA TAAGGCAAAA         240

AGGGATAAGA CTTCTGCAGA GCTTTATGCG CAAATTCCCC TTATCGAAGA AATCCTGTGT         300

GCACTGGGCA TTACAGTTTT GCGTCATGAC GGCTTTGAAG CTGACGACCT CATTGCAACC         360

CTAGCAAAAC GAGTTGCGGC TGAGCACTGT CATGTTGTGA TTATCTCCTC AGATAAAGAT         420

GTACTTCAGC TTGTGTGTGA TACGGTGCAA GTGCTCAGAC TTGACATAGA TCATAAGTGG         480

ACATGTTGCG ACGCTGCGTA CGTACAGCAA CGGTGGACGG TCATGCCAAC ACAATTACTT         540

GATTTGTTCT CTCTCATGGG AGATTCCTCC GACAATGTGC CTGGTGTGAG AGGGATTGGT         600

CCTAAGACGG CTGCACATCT TCTCCACTGT TTTGGCACAC TTGATGGTAT TTATCGTCAT         660

ACCTATTCCT TAAAAGAAGC GCTGCGCACG AAGATAGTGT GTGGGAAGAA AGATGCATTT         720

TTTTCTCGTT CACTCATTGA GTTGCGTGAC GATGTACCAT GTGTTTTTC GCTCGAAGAT          780

TCCTGTTGTA TTCCGCTCGA TGTAACGTCT GCTGCACGTA TTTTTGTGCG AGAAGGATTG         840

CATGCGCTTG CACAACAATA TCGTGCTTGT GTGCAAGAAA TAGATACAGA AGCAACAAAC         900

GATACATTAC AAATGACAGA GTCTTCTGTG CTCACGTCTG GTCGATGTGC AAATGAGTGT         960

TTCTTATCTC AGGTAGAAGG GAGGGCTAGT ACACCGGAGG TGAACTCCGT ATTGAAGTCG        1020
```

```
GAGTTGAAGA CGAGTGCTGT GTCTGGCGCC ATACCTATAG AAAATAGAGA TCTTAGGCAG      1080

GATGTTATGC TTGCACGCAG TGCAGGTCAT TATCGTGGTG TTACTGACCC TGTAGAACTT      1140

AAACGTATTA TTGATTGCGC GTGTGCGAAT GGTGTGGTCG CGTTTGATTG TGAAACGGAT      1200

GGATTGCATC CGCACGATAC ACGTCTGGTC GGATTTTCGA TCTGCTTTCA GGAAGCAGAG      1260

GCTTTTTATG TTCCTCTTAT TGTTCCGGAC GTTTCTCTTC ATACCGAGTC AACTCAGTGT      1320

ACATGTGCAC GTAGCACTAA TGTCGAGACT GAAAAGGAGT GCACAGAACA GCATGGGTA       1380

TCTGCATCTG CTGTGCAGGA TCCGGCATAT GTCCAAGCTG TCATGCACCA GCTTCGACGT      1440

CTTTGGAATG ATGAGACGCT CACACTTGTT ATGCATAATG GAAAGTTTGA TTATCACGTT      1500

ATGCATCGTG CAGGCGTTTT TGAGCACTGT GCATGTAATA TTTTCGATAC GATGGTTGCA      1560

GCTTGGTTGC TGGATCCCGA TCGCGGTACA TACGGTATGG ATGTACTTGC CGCATCATTC      1620

TTTCAGATCA GAACGATTAC ATTTGAAGAA GTGGTAGCAA AAGGGCAAAC CTTTGCGCAC      1680

GTCCCTTATG AGTGTGCAGT CCGCTATGCA GCGGAGGATG CAGATATTAC TTTTCGTTTA      1740

TACCATTATT TAAAACTCCG CTTGGAAACA GCAGGATTGC TTTCTGTGTT TGAGACCATA      1800

GAAATGCCGC TTTTGCCTAT CCTAGCACGT ATGGAAGAAG TGGGGATTTT TTTACGTAAG      1860

GATGTTGTGC AGCAGCTCAC TCGATCTTTT TCAGATTTGA TCCAGCAGTA CGAGCACGAT      1920

ATTTTTTCTC TTGCCGGTCA TGAATTTAAT ATTGGTTCTC CGAAGCAACT GCAGACAGTC      1980

CTTTTTCAAG AATTACATTT ACCGCCCGGT AAAAGAATA CTCAAGGTTA TTCTACTGAT       2040

CATTCTGTAT TGAAGAAACT TGCACGTAAG CATCCCATTG CAGAAAAAAT ATTGCTCTTT      2100

AGAGATCTTT CAAAGTTACG TTCGACGTAT ACCGAATCGC TTGCAAAACT TGCTGATCAA      2160

ACAGGGCGTG TACATACTAG CTTTGTGCAA ATTGGTACCC CAACTGGAAG GCTTTCGAGT      2220

AGAAATCCAA ATTTACAAAA CATTCCCATT AAAAGCACAG AAGGAAGAAA AATAAGGCAG      2280

GCGTTTCAAG CTACTGTTGG GCATGAGTTA ATTTCGGCAG ACTATACACA AATAGAGCTG      2340

GTCGCGTTGG CCCATCTATC TCAAGATAGA AATCTTCTCA ATGCATTTCG ACAGCACATT      2400

GATATTCATG CATTGACTGC TGCATATATT TTCAATGTGT CTATAGACGA TGTACAACCT      2460

GCAATGAGAA GAATCGCAAA AACTATTAAC TTTGGAATCG TGTATGGAAT GAGCGCTTTT      2520

AGATTGAGTG ACGAACTTAA AATTTCTCAG AAGGAAGCGC AGAGCTTCAT TTACCGTTAT      2580

TTTGAAACGT ACCCGGGGGT GTATGCTTTT AGTACACAGG TTGCAGAGCA GACACGTAAA      2640

ACCGGCTATG TGACTAGCTT GGCTGGAAGA CGACGCTACA TCCGTACTAT CGATAGTCGC      2700

AATACGCTTG AGCGCGCGCG TGCCGAACGT ATGGCGTTGA ATACTCAAAT TCAGAGTTCT      2760

GCGGCGGATA TTGTGAAAAT TGCCATGATA GCAATCCAGC GTGCGTTTGC GCGCCGACCG      2820

TTACGTGCAC AATTGTTGCT GCAGGTACAC GATGAATTGA TTTTTGAGGC GCCAGCTGCT      2880

GAGACAGCGA TAGTGAAAGA AATTCTCTTT GCTGAGATGG AACATGCTGT TGAGCTCTCG      2940

ATCCCGCTGC GTATACACGT GGAGTCTGGA AATAGTTGGG GTGATTTTCA T              2991
```

(2) INFORMATION FOR SEQ ID NO:2:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:2:

Gly Arg Cys Ala Asn Glu Cys Phe Leu Ser Gln Val Glu Gly Arg Ala
1               5                   10                  15

Ser Thr Pro Glu Val Asn Ser Val Leu Lys Ser Glu Leu Lys Thr Ser
            20                  25                  30

Ala Val Ser Gly Ala Ile Pro Ile Glu Asn Arg Asp Leu Arg Gln Asp
        35                  40                  45

Val Met Leu Ala Arg
        50

(2) INFORMATION FOR SEQ ID NO:3:

(i) SEQUENCE CHARACTERISTICS:
            (A) LENGTH: 40 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:3:

Ile Val Pro Asp Val Ser Leu His Thr Glu Ser Thr Gln Cys Thr Cys
1               5                   10                  15

Ala Arg Ser Thr Asn Val Glu Thr Glu Lys Glu Cys Thr Glu Gln His
            20                  25                  30

Gly Val Ser Ala Ser Ala Val Gln
        35                  40

(2) INFORMATION FOR SEQ ID NO:4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

TGCGCGTGTG CGAATGGTGT GGTC                                                24

(2) INFORMATION FOR SEQ ID NO:5:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

CACAGTGCTC AAAAACGCCT GCACG                                               25

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

TGTTTCTTAT CTCAGGTAGA AGGG                                    24

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

ACATGTACAC TGAGTTGACT CGG                                     23

(2) INFORMATION FOR SEQ ID NO:8:

(i) SEQUENCE CHARACTERISTICS:
        (A) LENGTH: 997 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:8:

```
Met Gln Glu Lys Lys Thr Leu Tyr Leu Leu Asp Ala Tyr Gly Leu Ile
 1               5                  10                  15

Tyr Arg Ser Tyr His Ala Phe Ala Arg Ala Pro Leu Ile Asn Asp Ser
                20                  25                  30

Gly Ala Asn Val Ser Ala Val Tyr Gly Phe Phe Arg Ser Leu His Thr
            35                  40                  45

Leu Leu Cys His Tyr Arg Pro Arg Tyr Phe Val Ala Val Phe Asp Ser
        50                  55                  60

Leu Thr Pro Thr Phe Arg His Val Gln Tyr Pro Ala Tyr Lys Ala Lys
65                  70                  75                  80

Arg Asp Lys Thr Ser Ala Glu Leu Tyr Ala Gln Ile Pro Leu Ile Glu
                85                  90                  95

Glu Ile Leu Cys Ala Leu Gly Ile Thr Val Leu Arg His Asp Gly Phe
            100                 105                 110

Glu Ala Asp Asp Leu Ile Ala Thr Leu Ala Lys Arg Val Ala Ala Glu
        115                 120                 125
```

-continued

```
His Cys His Val Val Ile Ile Ser Ser Asp Lys Asp Val Leu Gln Leu
    130                 135                 140

Val Cys Asp Thr Val Gln Val Leu Arg Leu Asp Ile Asp His Lys Trp
145                 150                 155                 160

Thr Cys Cys Asp Ala Ala Tyr Val Gln Gln Arg Trp Thr Val Met Pro
                165                 170                 175

Thr Gln Leu Leu Asp Leu Phe Ser Leu Met Gly Asp Ser Ser Asp Asn
            180                 185                 190

Val Pro Gly Val Arg Gly Ile Gly Pro Lys Thr Ala Ala His Leu Leu
        195                 200                 205

His Cys Phe Gly Thr Leu Asp Gly Ile Tyr Arg His Thr Tyr Ser Leu
    210                 215                 220

Lys Glu Ala Leu Arg Thr Lys Ile Val Cys Gly Lys Lys Asp Ala Phe
225                 230                 235                 240

Phe Ser Arg Ser Leu Ile Glu Leu Arg Asp Asp Val Pro Cys Val Phe
                245                 250                 255

Ser Leu Glu Asp Ser Cys Cys Ile Pro Leu Asp Val Thr Ser Ala Ala
            260                 265                 270

Arg Ile Phe Val Arg Glu Gly Leu His Ala Leu Ala Gln Gln Tyr Arg
        275                 280                 285

Ala Cys Val Gln Glu Ile Asp Thr Glu Ala Thr Asn Asp Thr Leu Gln
    290                 295                 300

Met Thr Glu Ser Ser Val Leu Thr Ser Gly Arg Cys Ala Asn Glu Cys
305                 310                 315                 320

Phe Leu Ser Gln Val Glu Gly Arg Ala Ser Thr Pro Glu Val Asn Ser
                325                 330                 335

Val Leu Lys Ser Glu Leu Lys Thr Ser Ala Val Ser Gly Ala Ile Pro
            340                 345                 350

Ile Glu Asn Arg Asp Leu Arg Gln Asp Val Met Leu Ala Arg Ser Ala
        355                 360                 365

Gly His Tyr Arg Gly Val Thr Asp Pro Val Glu Leu Lys Arg Ile Ile
    370                 375                 380

Asp Cys Ala Cys Ala Asn Gly Val Val Ala Phe Asp Cys Glu Thr Asp
385                 390                 395                 400

Gly Leu His Pro His Asp Thr Arg Leu Val Gly Phe Ser Ile Cys Phe
                405                 410                 415

Gln Glu Ala Glu Ala Phe Tyr Val Pro Leu Ile Val Pro Asp Val Ser
            420                 425                 430

Leu His Thr Glu Ser Thr Gln Cys Thr Cys Ala Arg Ser Thr Asn Val
        435                 440                 445

Glu Thr Glu Lys Glu Cys Thr Glu Gln His Gly Val Ser Ala Ser Ala
    450                 455                 460

Val Gln Asp Pro Ala Tyr Val Gln Ala Val Met His Gln Leu Arg Arg
465                 470                 475                 480

Leu Trp Asn Asp Glu Thr Leu Thr Leu Val Met His Asn Gly Lys Phe
                485                 490                 495

Asp Tyr His Val Met His Arg Ala Gly Val Phe Glu His Cys Ala Cys
            500                 505                 510

Asn Ile Phe Asp Thr Met Val Ala Ala Trp Leu Leu Asp Pro Asp Arg
        515                 520                 525

Gly Thr Tyr Gly Met Asp Val Leu Ala Ala Ser Phe Phe Gln Ile Arg
    530                 535                 540
```

-continued

```
Thr Ile Thr Phe Glu Glu Val Ala Lys Gly Gln Thr Phe Ala His
545                 550                 555                 560

Val Pro Tyr Glu Cys Ala Val Arg Tyr Ala Glu Asp Ala Asp Ile
                565                 570                 575

Thr Phe Arg Leu Tyr His Tyr Leu Lys Leu Arg Leu Glu Thr Ala Gly
            580                 585                 590

Leu Leu Ser Val Phe Glu Thr Ile Glu Met Pro Leu Leu Pro Ile Leu
        595                 600                 605

Ala Arg Met Glu Glu Val Gly Ile Phe Leu Arg Lys Asp Val Val Gln
610                 615                 620

Gln Leu Thr Arg Ser Phe Ser Asp Leu Ile Gln Gln Tyr Glu His Asp
625                 630                 635                 640

Ile Phe Ser Leu Ala Gly His Glu Phe Asn Ile Gly Ser Pro Lys Gln
                645                 650                 655

Leu Gln Thr Val Leu Phe Gln Glu Leu His Leu Pro Pro Gly Lys Lys
            660                 665                 670

Asn Thr Gln Gly Tyr Ser Thr Asp His Ser Val Leu Lys Lys Leu Ala
        675                 680                 685

Arg Lys His Pro Ile Ala Glu Lys Ile Leu Leu Phe Arg Asp Leu Ser
690                 695                 700

Lys Leu Arg Ser Thr Tyr Thr Glu Ser Leu Ala Lys Leu Ala Asp Gln
705                 710                 715                 720

Thr Gly Arg Val His Thr Ser Phe Val Gln Ile Gly Thr Ala Thr Gly
                725                 730                 735

Arg Leu Ser Ser Arg Asn Pro Asn Leu Gln Asn Ile Pro Ile Lys Ser
            740                 745                 750

Thr Glu Gly Arg Lys Ile Arg Gln Ala Phe Gln Ala Thr Val Gly His
        755                 760                 765

Glu Leu Ile Ser Ala Asp Tyr Thr Gln Ile Glu Leu Val Ala Leu Ala
770                 775                 780

His Leu Ser Gln Asp Arg Asn Leu Leu Asn Ala Phe Arg Gln His Ile
785                 790                 795                 800

Asp Ile His Ala Leu Thr Ala Ala Tyr Ile Phe Asn Val Ser Ile Asp
                805                 810                 815

Asp Val Gln Pro Ala Met Arg Arg Ile Ala Lys Thr Ile Asn Phe Gly
            820                 825                 830

Ile Val Tyr Gly Met Ser Ala Phe Arg Leu Ser Asp Glu Leu Lys Ile
        835                 840                 845

Ser Gln Lys Glu Ala Gln Ser Phe Ile Tyr Arg Tyr Phe Glu Thr Tyr
850                 855                 860

Pro Gly Val Tyr Ala Phe Ser Thr Gln Val Ala Glu Gln Thr Arg Lys
865                 870                 875                 880

Thr Gly Tyr Val Thr Ser Leu Ala Gly Arg Arg Tyr Ile Arg Thr
                885                 890                 895

Ile Asp Ser Arg Asn Thr Leu Glu Arg Ala Arg Ala Glu Arg Met Ala
            900                 905                 910

Leu Asn Thr Gln Ile Gln Ser Ser Ala Ala Asp Ile Val Lys Ile Ala
        915                 920                 925

Met Ile Ala Ile Gln Arg Ala Phe Ala Arg Arg Pro Leu Arg Ala Gln
930                 935                 940

Leu Leu Leu Gln Val His Asp Glu Leu Ile Phe Glu Ala Pro Ala Ala
945                 950                 955                 960

Glu Thr Ala Ile Val Lys Glu Ile Leu Phe Ala Glu Met Glu His Ala
```

```
                  965                 970                 975
Val Glu Leu Ser Ile Pro Leu Arg Ile His Val Glu Ser Gly Asn Ser
                980                 985                 990

Trp Gly Asp Phe His
        995
```

(2) INFORMATION FOR SEQ ID NO:9:

(i) SEQUENCE CHARACTERISTICS:
        (A) LENGTH: 3885 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
GACGCATACA CGCTCCTCCC CTTTAGTAAC ACGCTGGTGT TGGTGGACGT CAGCGGTGCA     60

GAGTTGAAAC AAATTATAGA GGATGCATTG CAGTTTGCAC TTGGTGATGG TTCCACGGGA    120

GCCTTCCCCT ATGGGCGGG TGTCCGGTAT GAAGCGCGCC AAGAACCAGA TGAACATGGC    180

AAACGAGTGA TAAAGCTTGA GGTGCAAAAA AAAGATGGAG CGTGGGTGCC AGTAAATGAG    240

CGCGCGCCGT ATCGGTTGGG TGTGAACTCG TACATTGCGC GGGGAAAAGA CGGATATAAA    300

ACGCTCGGAG AGATTGTCAG TACGCGCGGA GCTGAGGATA CGTATCTGCG TGATGCGGAG    360

TCTTTGATTA AGTTTTTGCG TGCGCATAAA AATTTTCGTG CATACACAGA TTCCAATGTG    420

ATATTCCGTC TTAAATAGTA GGAAGTAACT TACATTAGAG GCCTGTAAAG AACTACGTTC    480

TTTACAGGCT GTGCCAATCT GCTTTTCCGG GAAAGACAAA GGGTATGCCA CGTTAGGAGC    540

GGAAAGAAGG GTGCTGCACA TAACCTTATC TTTGCGATTG ACCGTGGTAT ACTCCTTGCA    600

CCTTATGCAA GAGAAAAAAA CGCTTTACCT TCTTGATGCC TACGGACTTA TTTATCGGAG    660

TTACCACGCG TTCGCGCGTG CGCCGTTGAT TAACGACAGC GGTGCGAATG TTTCTGCCGT    720

ATATGGTTTT TTTCGGAGTT TGCACACGCT CCTGTGTCAC TATCGACCCC GTTATTTTGT    780

TGCTGTTTTT GATTCTCTCA CGCCTACCTT TCGGCACGTA CAGTACCCAG CCTATAAGGC    840

AAAAAGGGAT AAGACTTCTG CAGAGCTTTA TGCGCAAATT CCCCTTATCG AAGAAATCCT    900

GTGTGCACTG GCATTACAG TTTTGCGTCA TGACGGCTTT GAAGCTGACG ACCTCATTGC    960

AACCCTAGCA AAACGAGTTG CGGCTGAGCA CTGTCATGTT GTGATTATCT CCTCAGATAA   1020

AGATGTACTT CAGCTTGTGT GTGATACGGT GCAAGTGCTC AGACTTGACA TAGATCATAA   1080

GTGGACATGT TGCGACGCTG CGTACGTACA GCAACGGTGG ACGGTCATGC AACACAATT   1140

ACTTGATTTG TTCTCTCTCA TGGGAGATTC CTCCGACAAT GTGCCTGGTG TGAGAGGGAT   1200

TGGTCCTAAG ACGGCTGCAC ATCTTCTCCA CTGTTTTGGC ACACTTGATG GTATTTATCG   1260

TCATACCTAT TCCTTAAAAG AAGCGCTGCG CACGAAGATA GTGTGTGGGA AGAAAGATGC   1320

ATTTTTTTCT CGTTCACTCA TTGAGTTGCG TGACGATGTA CCATGTGTTT TTTCGCTCGA   1380

AGATTCCTGT TGTATTCCGC TCGATGTAAC GTCTGCTGCA CGTATTTTTG TGCGAGAAGG   1440

ATTGCATGCG CTTGCACAAC AATATCGTGC TTGTGTGCAA GAAATAGATA CAGAAGCAAC   1500

AAACGATACA TTCAAATGA CAGAGTCTTC TGTGCTCACG TCTGGTCGAT GTGCAAATGA   1560

GTGTTTCTTA TCTCAGGTAG AAGGGAGGGC TAGTACACCG GAGGTGAACT CCGTATTGAA   1620
```

-continued

```
GTCGGAGTTG AAGACGAGTG CTGTGTCTGG CGCCATACCT ATAGAAAATA GAGATCTTAG    1680

GCAGGATGTT ATGCTTGCAC GCAGTGCAGG TCATTATCGT GGTGTTACTG ACCCTGTAGA    1740

ACTTAAACGT ATTATTGATT GCGCGTGTGC GAATGGTGTG GTCGCGTTTG ATTGTGAAAC    1800

GGATGGATTG CATCCGCACG ATACACGTCT GGTCGGATTT TCGATCTGCT TTCAGGAAGC    1860

AGAGGCTTTT TATGTTCCTC TTATTGTTCC GGACGTTTCT CTTCATACCG AGTCAACTCA    1920

GTGTACATGT GCACGTAGCA CTAATGTCGA GACTGAAAAG GAGTGCACAG AACAGCATGG    1980

GGTATCTGCA TCTGCTGTGC AGGATCCGGC ATATGTCCAA GCTGTCATGC ACCAGCTTCG    2040

ACGTCTTTGG AATGATGAGA CGCTCACACT TGTTATGCAT AATGGAAAGT TGATTATCA     2100

CGTTATGCAT CGTGCAGGCG TTTTTGAGCA CTGTGCATGT AATATTTTCG ATACGATGGT    2160

TGCAGCTTGG TTGCTGGATC CCGATCGCGG TACATACGGT ATGGATGTAC TTGCCGCATC    2220

ATTCTTTCAG ATCAGAACGA TTACATTTGA AGAAGTGGTA GCAAAAGGGC AAACCTTTGC    2280

GCACGTCCCT TATGAGTGTG CAGTCCGCTA TGCAGCGGAG GATGCAGATA TTACTTTTCG    2340

TTTATACCAT TATTTAAAAC TCCGCTTGGA AACAGCAGGA TTGCTTTCTG TGTTTGAGAC    2400

CATAGAAATG CCGCTTTTGC CTATCCTAGC ACGTATGGAA GAAGTGGGGA TTTTTTTACG    2460

TAAGGATGTT GTGCAGCAGC TCACTCGATC TTTTTCAGAT TTGATCCAGC AGTACGAGCA    2520

CGATATTTTT TCTCTTGCCG GTCATGAATT TAATATTGGT TCTCCGAAGC AACTGCAGAC    2580

AGTCCTTTTT CAAGAATTAC ATTTACCGCC CGGTAAAAAG AATACTCAAG GTTATTCTAC    2640

TGATCATTCT GTATTGAAGA AACTTGCACG TAAGCATCCC ATTGCAGAAA AATATATTGCT   2700

CTTTAGAGAT CTTTCAAAGT TACGTTCGAC GTATACCGAA TCGCTTGCAA AACTTGCTGA    2760

TCAAACAGGG CGTGTACATA CTAGCTTTGT GCAAATTGGT ACCGCAACTG GAAGGCTTTC    2820

GAGTAGAAAT CCAAATTTAC AAAACATTCC CATTAAAAGC ACAGAAGGAA GAAAAATAAG    2880

GCAGGCGTTT CAAGCTACTG TTGGGCATGA GTTAATTTCG GCAGACTATA CACAAATAGA    2940

GCTGGTCGCG TTGGCCCATC TATCTCAAGA TAGAAATCTT CTCAATGCAT TTCGACAGCA    3000

CATTGATATT CATGCATTGA CTGCTGCATA TATTTTCAAT GTGTCTATAG ACGATGTACA    3060

ACCTGCAATG AGAAGAATCG CAAAAACTAT TAACTTTGGA ATCGTGTATG AATGAGCGC     3120

TTTTAGATTG AGTGACGAAC TTAAAATTTC TCAGAAGGAA GCGCAGAGCT TCATTTACCG    3180

TTATTTTGAA ACGTACCCGG GGGTGTATGC TTTTAGTACA CAGGTTGCAG AGCAGACACG    3240

TAAAACCGGC TATGTGACTA GCTTGGCTGG AAGACGACGC TACATCCGTA CTATCGATAG    3300

TCGCAATACG CTTGAGCGCG CGCGTGCCGA ACGTATGGCG TTGAATACTC AAATTCAGAG    3360

TTCTGCGGCG GATATTGTGA AAATTGCCAT GATAGCAATC CAGCGTGCGT TTGCGCGCCG    3420

ACCGTTACGT GCACAATTGT TGCTGCAGGT ACACGATGAA TTGATTTTTG AGGCGCCAGC    3480

TGCTGAGACA GCGATAGTGA AAGAAATTCT CTTTGCTGAG ATGGAACATG CTGTTGAGCT    3540

CTCGATCCCG CTGCGTATAC ACGTGGAGTC TGGAAATAGT TGGGGTGATT TCATTAGCA     3600

TACCCATCTG AGGGATGCAA CAGGGCACGT TATGAGGTTA CCTCGGCGCG TAGTTCCTTA    3660

AAAAATGATG CTACCACGCA CAACATAATC AGCGCTAAAG GAAATGCCGC AATGATGGCT    3720

AAACTTTTCA GGTGCATGAG TGTGGACTGG GAGAATATGA GAGAAGCGGG AAGGAGAATG    3780

CACGCAACCG CCCAAAACGA TTTCATTATT TGACGTGGTT CTTCTACCCG GTGCAACGCT    3840

TTTTTGCGAA TAGGAAGCGA TGATGAGCGT TAATGCGTCA AAAGT                    3885
```

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

CCCGAATTCT GTGCCAATCT GCTTTTCCGG                                              30

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

TGAAAAGCTT GGTAACCTCA TAACGTGCCC T                                            31

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:12:

Gln Glu Ile Asp Thr Glu Ala Thr Asn Asp Thr Leu Gln Met Thr Glu
1               5                  10                  15

Ser Ser Val Leu
            20

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:13:

Ser Gln Val Glu Gly Arg Ala Ser Thr Pro Glu Val Asn Ser Val Leu
1               5                  10                  15

Lys Ser Glu Leu

-continued

```
            20

(2) INFORMATION FOR SEQ ID NO:14:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:14:

Val Leu Lys Ser Glu Leu Lys Thr Ser Ala Val Ser Gly Ala Ile Pro
1               5                  10                 15

Ile Glu Asn Arg
            20
```